United States Patent [19]

Wegman et al.

[11] Patent Number: 5,026,907

[45] Date of Patent: Jun. 25, 1991

[54] PRODUCTION OF CARBOXYLIC ACIDS FROM ALCOHOLS USING RHODIUM COMPLEX CATALYSTS AND ORGANIC ESTER SOURCE

[75] Inventors: Richard W. Wegman, South Charleston; David J. Schreck, Cross Lanes, both of W. Va.

[73] Assignee: Union Carbide Chemicals and Plastics Technology Corporation, Danbury, Conn.

[21] Appl. No.: 794,606

[22] Filed: Nov. 6, 1985

Related U.S. Application Data

[63] Continuation-in-part of Ser. No. 641,477, Aug. 16, 1984, abandoned.

[51] Int. Cl.$^5$ .................. C07C 51/12; C07C 53/08; C07C 53/12
[52] U.S. Cl. .................. 562/519; 562/517; 562/891
[58] Field of Search .................. 562/519, 517, 891; 260/413, 549

[56] References Cited

U.S. PATENT DOCUMENTS

| | | | |
|---|---|---|---|
| 1,697,109 | 1/1929 | Dreyfus | 562/607 |
| 3,060,233 | 10/1962 | Hohenschutz | 562/519 |
| 3,769,329 | 10/1973 | Paulik et al. | 562/519 |
| 4,194,056 | 3/1980 | Antoniades | 562/519 |
| 4,212,989 | 7/1980 | Isshiki et al. | 562/519 |

FOREIGN PATENT DOCUMENTS

| | | |
|---|---|---|
| 0002557 | 6/1979 | European Pat. Off. |
| 0018927 | 11/1980 | European Pat. Off. |
| 2317269 | 2/1977 | France |
| WO80/00213 | 8/1980 | PCT Int'l Appl. |
| 1326014 | 8/1973 | United Kingdom .......... 562/519 |
| 1584740 | 2/1981 | United Kingdom |

OTHER PUBLICATIONS

Applied Industrial Catalysis; vol. 1, Chapter 10, pp. 275 and 281, Academic Press, NYC (1981).
"Bidentate Amine N-Oxides and Phosphine Oxides as Ligands in Rhodium (I) Chemistry", Uson et al., *Journal of Organometallic Chemistry*, 240, 429–439 (1982).

*Primary Examiner*—Vivian Garner
*Attorney, Agent, or Firm*—Henry H. Gibson

[57] ABSTRACT

A process for the production of organic carboxylic acids and organic carboxylic acid anhydrides by the catalytic reaction of an alcohol of the formula ROH and carbon monoxide in contact with an organic ester source and a homogeneous catalyst system of rhodium metal atom, a phosphorus containing ligand in which there is present at least one oxo (=O) oxygen atom attached to a phosphorus atom or a carbon atom to form a Z group and the

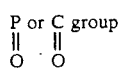

in said Z group is located at least one carbon atom removed and preferably from 2–4 carbon atoms removed from the phosphorus atom of the molecules represented by the formulas

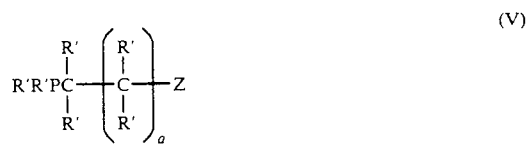

(V)

or

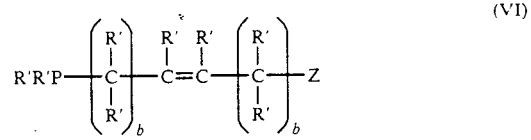

(VI)

and a halogen source, under mild reaction conditions, wherein R' is -H, aryl, alkaryl, aralkyl or alkyl, and wherein 1 or more of said R' groups can be substituted with a Z group but not more than 3 of said R' groups in the molecule are so substituted; a is an integer from 0–4; b is an integer from 0–3; and Z is P(O)R'R'; —C(O)OR" or C(O)R", wherein R" is R'; and wherein ROH is methanol or a mixture of methanol and at least one higher alcohol.

20 Claims, No Drawings

PRODUCTION OF CARBOXYLIC ACIDS FROM ALCOHOLS USING RHODIUM COMPLEX CATALYSTS AND ORGANIC ESTER SOURCE

This application is a continuation-in-part of prior U.S. application Ser. No. 641,477 filing date Aug. 16, 1984, now abandoned.

BACKGROUND OF THE INVENTION

The production of organic compounds using synthesis gas, which is a mixture of carbon monoxide and hydrogen, or from carbon monoxide as one of the reactants has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that alcohols, esters, ethers, and other organic compounds can be reacted with synthesis gas or carbon monoxide to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as the catalyst and a halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of acetic acid, to our knowledge it does not disclose or suggest our invention. Several of the pertinent patents in this area are discussed below.

French patent No. 2,317,269, filed by Compagnie Des Metaux Precieux and published on Feb. 4, 1977, discloses the production of aliphatic carboxylic acids by the reaction of an alcohol with carbon monoxide in the presence of a catalyst containing at least three essential components, iridium atom, copper atom and halogen. This is not our process.

In European patent application No. 0,018,927; filed by Gauthier-Lafaye et al on Apr. 23, 1980 and published on Nov. 12, 1980, there is described a process for the production of monocarboxylic acids by the carbonylation of an alcohol using a nickel catalyst, a halide and a solvent. In the instant process an organic acid is produced from an alcohol and carbon monoxide in contact with an organic ester source using a rhodium complex as the catalyst and a specific halogen source, such as lithium iodide and methyl iodide.

U.S. Pat. No. 3,060,233, issued to Hohenschutz on Oct. 23, 1962, discloses the carbonylation of methanol to acetic acid using a metal of the iron group of the Periodic Table and a halide. It does not disclose use of the instant rhodium complex at the mild pressure and temperature conditions employed herein.

U.S. Pat. No. 3,769,329, issued Oct. 30, 1973 to Paulik et al, discloses the use of a conventional rhodium catalyst and conventional ligands. The preferred mode of operation of this prior art process requires a large excess of water to ensure selectivity to acetic acid. This reference employs relatively extreme reaction conditions of temperature and pressure, and makes no distinction relating to the suitability of useful ligands or halogen sources.

U.S. Pat. No. 4,212,989, issued to Isshiki et al., on Jul. 15, 1980, describes a process for producing carboxylic acids or their esters by reacting an alcohol or an ether with carbon monoxide using a Group VIII metal catalyst and an iodine promoter. The reference contains no disclosure or suggestion of the production of organic carboxylic acids employing a specific rhodium complex under mild reaction conditions.

British patent specification No. 1,584,740, issued Feb. 18, 1981 to Air Products relates to the production of acetic acid at more extreme reaction conditions using a different ligand, shown by us to be ineffective under the mild reaction conditions of this invention.

Another known procedure for producing acetic acid is the catalytic isomerization of methyl formate as shown by the reaction:

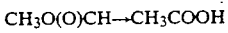

$$CH_3O(O)CH \rightarrow CH_3COOH$$

This procedure is shown in U.S. Pat. No. 1,697,109, issued to Henry Dreyfuss on Jan. 1, 1929. The process described is a vapor phase isomerization reaction caried out at 200° C. to 450° C. at a pressure, for example, on the order of 200 atmospheres using a metal oxide or acetate catalyst. That is typical of the extreme reaction conditions normally used in this area of technology. The reference does not disclose the use of alcohols as starting materials.

U.S. Pat. No. 4,194,056, filed by Antoniades and issued Mar. 18, 1980, discloses the production of carboxylic acid from methyl formate using a soluble rhodium catalyst, halogen promoter and carbon monoxide. This is not the process of the instant invention, nor does this reference disclose or suggest the use of a specific rhodium complex, the instant mild reaction conditions or the specific halogen source employed herein nor the unexpected results achieved by their use.

It can be seen that the prior art contains many disclosures dealing with the catalytic production of acetic acid, including its production from methanol. The art also discloses the production of other organic carboxylic acids from other alcohols. One of the disadvantages of many of these reference processes is the presence of water with the eventual need to remove it from the desired organic acid product. This removal is both complicated and costly. The process of this invention generates anhydrous carboxylic acids and essentially eliminates this problem.

Frequently, as shown above, typical prior art processes employing rhodium catalyst to produce acetic acid, require rather harsh reaction conditions of temperature and pressure to obtain satisfactory yields of products. Such reaction conditions require use of expensive reactors, engender excessive energy cost, often lead to undesired by-products and cause excessive corrosion problems.

Many processes employed for the production of organic acids use a catalyst system containing a source of metal atom and a source of halide atom. The alkali metal halides are often mentioned as suitable halide sources, but no distinction is made between any specific one of the alkali metal halides or between any other halogen compound. Nor do any of the references suggest or recognize the unexpected advantage of the use of mixtures of lithium iodide and methyl iodide in conjunction with rhodium catalyst.

SUMMARY OF THE INVENTION

A process for the production of organic acids at high efficiency, selectivity and conversion rate by the reaction of mixtures of alcohol and an ester or a compound which under the reaction conditions can be converted to an ester (e.g. acetic acid, acetic anhydride, methyl formate) and carbon monoxide has been found. The catalyst system charged to the reactor in the process contains rhodium atoms, a halogen source of the invention, and an organic ligand. The use of a halogen source, such as mixtures of lithium iodide and methyl iodide, in this system within the ranges defined results in unexpectedly high efficiency, high conversion rate or activity and high selectivity of anhydrous carboxylic acids not heretofore achieved at such mild operating conditions.

In a preferred embodiment the process can produce acids of the formula RCOOH, wherein R is a monovalent hydrocarbyl group, preferably on alkyl group having 1 to 10 carbon atoms. The process includes the catalytic reaction of an alcohol of the formula ROH and carbon monoxide in contact with an organic ester of the formula RC(O)OR or a compound which, under the reaction conditions, can be converted to the organic ester and a homogeneous catalyst system, at mild reaction conditions.

The catalyst system of this invention consists essentially of rhodium metal atom and a phosphorus containing ligand in which there is present at least one oxo (=O) oxygen atom attached to a phosphorus atom or a carbon atom to form a Z group and the

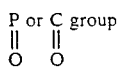

in said Z group is located at least one carbon atom removed and preferably from 2-4 carbon atoms removed from the phosphorus atom of the molecules represented by the formulas

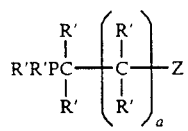

or

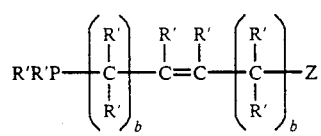

and a halogen source, wherein R' is hydrogen or unsubstituted or substituted (e.g. halogen, nitro, amino, etc.) aryl, aralkyl or alkaryl having from 6 to 10 ring carbon atoms and the alkyl moiety of the aralkyl or alkaryl group has from 1 to 10 carbon atoms and preferably 1 to 4 carbon atoms; or alkyl having from 1 to 10 carbon atoms and preferably 1 to 4 carbon atoms; and wherein 1 or more of said R' groups can be substituted with a Z group but not more than 3 of said R' groups in the molecule are so substituted; a is an integer from 0-4; b is an integer from 0-3; and Z is a member selected from the group consisting of

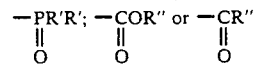

wherein R" is R'. R' can be same or different.

The halogen source is a metal halide, preferably lithium iodide, or a mixture of the metal halide and a halide promoter, preferably hydriodic acid or methyl iodide.

The reaction conditions are mild, usually at reaction temperatures less than about 150° C. and at reaction pressures less than about 250 psig. The reaction process can be carried out at a reaction temperature up to about 170° and a reaction pressure up to about 450 psig.

Under catalytic conditions it is understood that a novel monocarbonyl rhodium complex of the formula A:

$$Rh(CO)X(R'R'PGZ) \qquad [A]$$

wherein X is halogen and R' and Z are as before, and wherein G represents the two

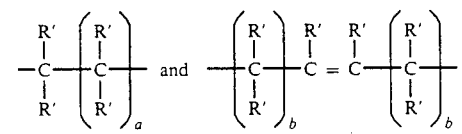

groups of formulas (V) and (VI), is formed in-situ.

The novel rhodium complex of the invention has been synthesized, isolated and characterized. The synthesized rhodium complex may be prepared in advance and used in place of the in-situ formed catalyst.

The Formula A rhodium complex is understood to be subject to the addition of a second mole of carbon monoxide to form a second catalytic dicarbonyl rhodium complex of Formula B and having the general formula:

$$Rh(CO)_2X(R'R'PGZ) \qquad [B]$$

The Formula B rhodium complex can be prepared in advance of the process rather than being formed in-situ from Formula [A].

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect.

Activity or conversion rate relates to the amount of reactants the catalyst converts to product per unit of time, generally expressed in g. mole per liter per hour (g mole/1/hr) or mole per hour (Mhr$^{-1}$).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective they usually require rather harsh reaction conditions and, accordingly, improvement is always desirable. Other factors having an impact on the process are the reaction temperature and reaction pressure. In the past it was generally thought necessary to increase these variables to improve overall selectivity and conversion.

The present invention is based on the unexpected and unpredictable discovery that the herein defined rhodium-catalyst systems which contain the specifically defined ligands and a defined halogen source produce essentially anhydrous organic acids from alcohols and carbon monoxide in conjunction with an ester or a compound which converts to one in-situ at unexpectedly high efficiency, selectivity and conversion rates at mild reaction conditions. Optionally, a solvent and/or diluent can also be present.

In the process of the invention certain alcohols are reacted with carbon monoxide in the presence of certain esters and the inventive catalyst system. This system produces commercially desirable essentially anhydrous organic acids at unexpectedly high efficiency, conversion rate and selectivity, with a minimum of by-products, without the presence of water and under mild reaction conditions. The overall reaction that occurs in the production of acids is theoretically:

$$ROH + CO \rightarrow RCOOH$$

Under this reaction scheme the ester introduced into the reactor is to all intents and purposes not consumed nor does the quantity thereof increase and it is recycled.

A further embodiment is the overall reaction that occurs when more than 1 mole of CO per mole of ROH is reacted. In such instance the excess CO will react with the ester present in the reaction mixture and one will obtain as the product an essentially anhydrous mixture of carboxylic acid and carboxylic anhydride. The amount of excess CO charged can be varied up to an amount sufficient to convert all of the ester to the anhydride. This overall reaction is theoretically:

$$ROH + RCOOR + 2CO \rightarrow RCOOH + RC(O)O(O)CR$$

In the above formulas R may be a monovalent hydrocarbyl group and preferably, an alkyl group having from 1 to 3 carbon atoms and, most preferably 1 carbon atom. The R group can be linear or branched and it can be unsubstituted or substituted with groups which will not have an adverse effect on the reaction. Among the suitable alcohols are methanol, ethanol and the propanols, with the preferred one being methanol. Among the suitable esters are methyl formate, methyl acetate, ethyl acetate, ethyl formate, methyl propionate, propyl acetate, ethyl propionate and the like.

The rhodium component of the catalyst system can be supplied from any number of sources, many of them are known to those of ordinary skill in the art. Thus, it is not necessary for an understanding thereof to specifically enumerate every suitable type and every specific compound since any of the known rhodium compounds can be used.

The essential rhodium component of the catalyst system of the present invention may be provided by introducing into the reaction zone a compound of rhodium or may be provided by introducing into the reaction zone, rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

$RhCl_2$
$RhBr_3$
$RhI_2$
$RhCl_3.3H_2O$
$RhBr_3.3H_2O$
$Rh_2(CO)_4Cl_2$
$Rh_2(CO)_4Br_2$
$Rh_2(CO)_4I_2$
$Rh_2(CO)_8$
Rh metal
$Rh(NO_3)_3$
$[(n-C_4H_9)_4N][Rh(CO)_2X_2]$ where X=Cl—, Br—, I—
$[(n-C_4H_9)_4As]_2[Rh(CO)_2Y_4]$ where X=Cl—, Br—, I—
$[(n-C_4H_9)_4P][Rh(CO)I_4]$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2(SnI_2)_4$ The rhodium metal atom concentration can vary over a wide range. Enough metal atom must be present to achieve reasonable reaction rates; however, an excess may, on occasion, result in undesired by-products formation. The mole ratio of rhodium atom to alcohol can vary from 1:25 to 1:20,000, the preferred range is from about 1:40 to 1:1000, with the most preferred range being from about 1:100 to 1:500. The amount used is not a critical feature in this invention and higher rhodium concentrations are acceptable but are influenced by economic considerations.

In general the rate of reaction increases with increasing rhodium concentration. For most purposes it is sufficient to employ a rhodium concentration from about 0.0001 to 1 mole per liter, preferably from about 0.01 to 0.1 mole per liter, although higher or lower concentrations may be utilized, depending, in part, upon economic considerations.

The second component of the catalyst system is a halogen source which contains a metal halide employed alone, or, more preferably, in combination with halide promoter. The metal halide, which is a Group I, II, V, VI, or VIII metal halide must be present. The preferred metal halide is a lithium halide.

The halide promoter component of the catalyst can be a halogen compound containing iodine, bromine or chlorine or two or more of the same, or the elemental halogen per se, or any mixtures of compounds and/or elements. Their identities are well known to those of ordinary skill in this art.

The preferred halide promoters are methyl iodide and iodine. As indicated, other suitable halogen compounds are well known to those of average skill in this art; thus a complete listing is not necessary for their comprehension.

The lithium halide can be charged directly to the process or it can be formed in-situ by any combination of lithium compound and halide component that will result in the formation of lithium halide during the reaction. Lithium bromide can also be used, but lithium iodide is the The presence of lithium iodide in conjunction with a halide promoter, such as methyl iodide is a preferred embodiment of this invention. Direct charge of lithium iodide is the preferred form. However, any convenient combination of compounds for in-situ formation of lithium iodide can be used. This includes the use of lithium carboxylates, carbonates and the like with a halogen compound such as iodine or an alkyl halide. A suitable combination for in-situ formation is lithium carboxylate (with the same functionality as the ester feed stock) and an alkyl halide.

Illustrative of suitable halogen sources there can be mentioned barium iodide, hydriodic acid, cobalt iodide, potassium iodide, lithium iodide, sodium iodide, calcium iodide, ammonium iodide, methyl iodide, ethyl iodide, propyl iodide, 2-ethylhexyl iodide, n-decyl iodide, acetyl iodide, propionyl iodide; the organic ammonium iodides of the formula $R'''_4NI$ and the organic phosphonium iodides of the formula $R'''_4PI$ in which $R'''$ is alkyl, saturated or unsaturated, substituted or unsubstituted, having from 1 to about 10 carbon atoms or aryl, unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetra-2-ethylhexyl phosphonium iodide, tetrapropyl phosphonium iodide, methyltriphenyl phosphonium iodide, and the like; methylammonium iodide, tri-p-tolyl-ammonium iodide, decylammonium iodide, ethylphosphonium iodide, triphenylphosphonium iodide, tricyclohexylphosphonium iodide, tri-p-tolylphosphonium iodide and the like. Also useful are bromine and its corresponding compounds and chlorine and its corresponding compounds. Any source of halogen atom can be used provided that it does not have a deleterious effect on the reaction.

The amount of halogen charged is dependent, in part, on the amount of rhodium employed. Sufficient halogen source must be present to exert a promoting effect on the reaction to enhance efficiency, conversion rate and selectivity to the corresponding organic acid. Where the halogen source is a lithium halide, such as lithium iodide, solely, the mole ratio of LiX:Rh may vary widely. For the preferred LiI, the mole ratio of LiI:Rh ranges from 1:200 to 200:1 and particularly from 1:1 to 128:1. When the halogen source is a mixture of, for example, lithium iodide and methyl iodide, then the same LiI:Rh ratio is maintained, and the CH$_3$I:LiI mole ratio ranges from 1:200 to 200:1 and more preferably, from 10:1 to 1:10.

The third component of the catalyst system is a phosphorus-containing ligand of the formula R'R'PGZ, wherein R' and G are as prevously defined and Z is selected from the group:

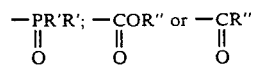

The R' aryl, aralkyl or alkaryl groups have from 6–10 ring carbon atoms. The alkyl moiety of the alkaryl or aralkyl group has from 1–10 carbon atoms, preferably 1–4 carbon atoms. The alkyl group has from 1 to 10 carbon atoms and preferably 1–4 carbon atoms.

In a first embodiment, the phosphorus-containing ligand has the general formula $$R'R'PGPR'R' \quad (I)$$

wherein R' and G are as before. The R' groups can be alike, different or mixed. Typical ligands of this embodiment include:

(1)

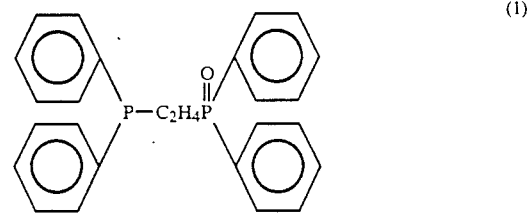
(2)

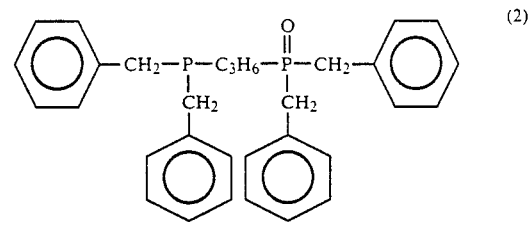
(3)

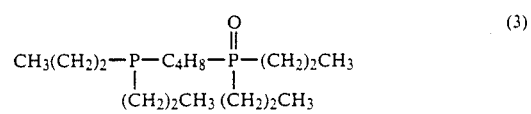
(4)

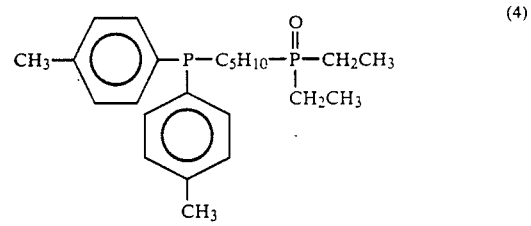
(5)

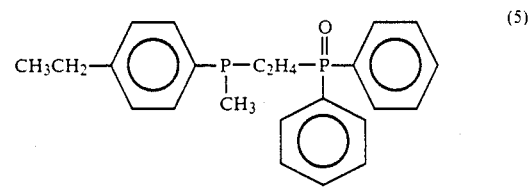
(6)

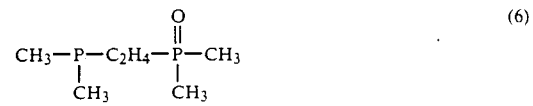

-continued

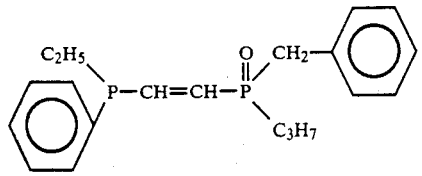 (7)

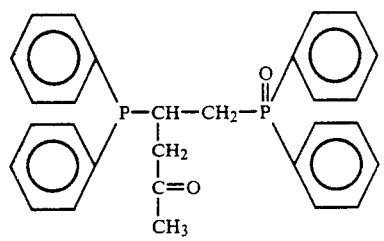 (8)

An especially preferred ligand of Formula (I) is

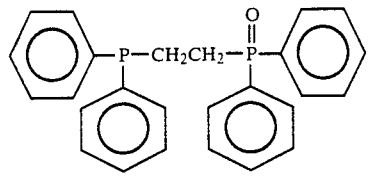

In a second embodiment the phosphorus-containing ligands have the general formula (II):

R'R'PGC(O)OR'' and in third embodiment the phosphorus-containing ligands have the general formula III:

wherein R' and G are as before; and R'' is R'.

Typical examples of formula II compounds include:

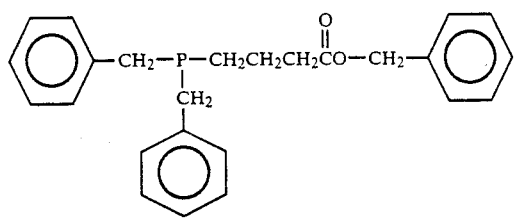 (a)

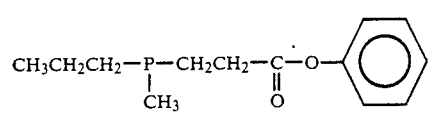 (b)

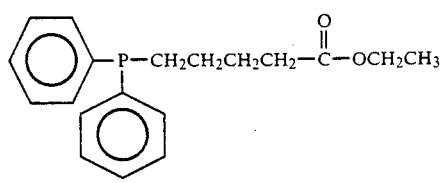 (c)

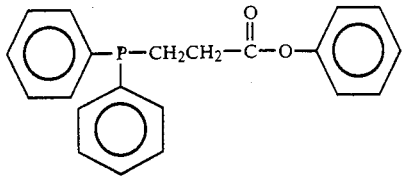 (d)

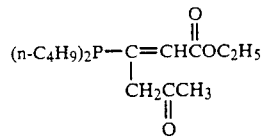 (e)

Typical examples of formula (III) compounds include:

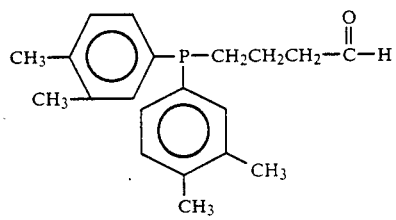 (f)

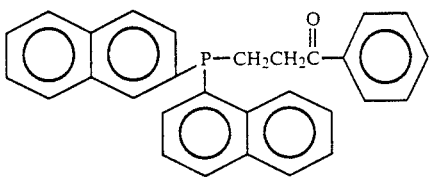 (g)

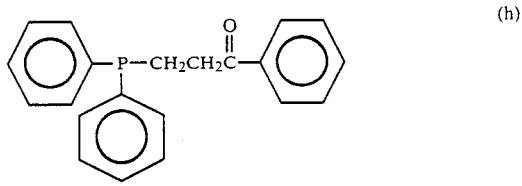 (h)

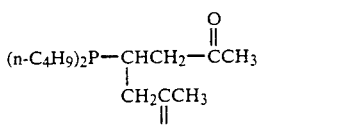 (i)

It has been found that certain conventional ligands such as the chelating agents, R'R'P(CH$_2$)$_n$PR'R' disclosed in U.K. Patent Specification Re. No. 1,584,740, tend to deactivate the catalyst system at low temperature and pressure.

It is believed important that the oxo (O═) group of the —P(O)—; —C(O)O— or —C(O)— moiety of Z may be capable of becoming bonded to the rhodium atom in order to provide the activated catalyst which permits rapid reaction with CO and halogen source to enhance the rate of reaction.

The reactive rhodium complex of formula A can be generally prepared and isolated by the typical reaction involving the dissolution of [Rh(CO)$_2$Cl]$_2$, or any other halide compound of this formula, in an inert solvent, such as dichloromethane, benzene, toluene and like, under inert atmospheric conditions. A stoichiometric amount of phosphine, based on the rhodium content, is added, and the mixture is stirred at a temperature of from about 0° C. or less up to the boiling point of the mixture, or higher. The reaction can be carried out at subatmospheric, atmospheric or superatmospheric pressure. The temperature and pressure are not critical.

Stirring is continued until the reaction is complete and this, as is obvious, will be dependent upon the specific reactants employed, reaction conditions used and the size of the batch. At completion of the reaction, one can, if so desired, separate the complex from the diluent using conventional procedures.

The structure of the formula A complex, identified herein as [A'] is believed to be (schematically) as follows:

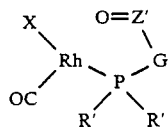

wherein R', G and X are as before and Z' is —P—R'R'; —COR" or —CR" and wherein R" is R'. The formula A complex may be formed in either the cis- or trans- geometrical isomer, wherein the X— and OC— moieties in complex A' are as they appear or are reversed.

Analysis to date of complex A' by NMR and IR has demonstrated the cis-isomer as the form present at room temperature.

In the catalytic reaction for the production of the essentially anhydrous caboxylic acids the catalyst complex can be prepared and then added to the reactor or it can be formed in-situ during the reaction.

Carbon monoxide may be combined with Formula A complexes to form Formula B complexes. That complex may be represented, schematically by Formula B' as follows:

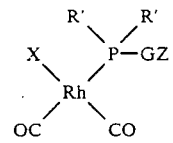

wherein X, R', G and Z are as before.

If desired, Formula B complexes may be prepared in advance of the process by the carbonylation of Formula A complexes or the like. Formula B complexes have not yet been isolated, but, from spectral analyses of the reaction mixture appear to have the indicated structure. Other procedures which will be apparent to those skilled in this art may also be utilized to make Formula B complexes.

The concentration of ligand charged to the catalytic reaction can be varied from a molar ratio of ligand to rhodium of from about 50:1 to 1:50, preferably from 10:1 to 1:10 and most preferably from about 3:1 to 1:1.

In addition to the ligand one can optionally have a solvent present. Many essentially inert solvents are known as useful, essentially inert, diluents and illustrative thereof one can mention 1,4-dioxane, the polyethylene glycol di-ethers or esters, diphenyl ether, sulfolane, toluene, carboxylic acids as well as any other diluent or solvent which does not interfere with the reaction to any significant extent. A preferred solvent is acetic acid. The use of acetic acid is especially beneficial in preventing precipitation of catalyst during more extended reaction times.

Essential to the invention is the presence in the reaction mixture of an organic ester or a compound which under reaction conditions can be converted to an organic ester. As previously indicated the ester can be recycled or it can be made to react. This will depend upon the amount of CO that is permitted to be consumed by the alcohol/ester feed. When the amount of CO consumed is the quantity sufficient to be consumed by the alcohol alone, or by the alcohol and a portion of the ester, unreacted ester is recycled. If the amount of CO consumed is sufficient to react with all the alcohol and ester there is no recycle. To avoid a more complex reaction mix, the organic moiety R of the ester RC(O)OR is preferably identical to the R moiety of the alcohol charged.

The ester can be charged directly or formed in-situ. For example, acetic acid can be charged which will generate the ester, methyl acetate, upon reaction with methanol. The preferred feed is methanol and methyl acetate.

In general the ratio of alcohol to ester can vary over a wide range. The volume ratio of alcohol to ester varies from about 100:1 to 1:100, preferably from 50:1 to 1:50 and most preferably from 10:1 to 1:10.

The reaction is carried out at a mild reaction temperatures, up to about 170° C. and preferably from about 50° C. to 160° C. and, most preferably, from 105° C. to 150° C.

The reaction pressure employed is much milder than those generally employed. The reaction pressure generally is up to about 450 psig and preferably, from 100 psig to 400 psig.

The reaction time varies depending upon the reaction parameters, reactor size and charge, and the individual components employed at the specific process conditions. The reaction can be a batch or continuous reaction.

PREPARATION EXAMPLE 1

The reactions were carried out in any convenient equipment for example a glass pressure bottle (Fisher Porter ®) or in a 150 cc or a 300 cc reaction autoclave. In the case of the glass bottle the reagents can be charged in numerous ways. For example, all the solid components (LiI, Rh, phosphine ligand) are first charged, the bottle is then purged with CO and methanol, methyl acetate and CH₃I are then added under a CO flow. Alternatively, a complex such as RhCO(I) [Ph₂PCH₂CH₂P(O)Ph₂] is dissolved in the liquid feed and then added to the bottle which contains LiI. In any event, once all the reagents are added, the bottle is pressured to 30 psi with CO, sealed by means of a valve, and heated to the desired temperature, usually between 105° and 125° C. At the desired temperature the pressure is adjusted to the reported value with CO. The bottle was repressurized after every 10 psi uptake. The reaction was typically carried out from 0.5 to 4.0 hours.

PREPARATION EXAMPLE 2

The following procedures were used with a 150 cc autoclave. The autoclave is equipped with a magnetically driven agitator, internal cooling coil, gas sampling port and electric heater. Prior to charging the reactants the autoclave is washed with methanol at 100° C. at 500–1,000 psia syn gas for 30 minutes. The reactor is drained, opened, rinsed with acetone, and dried with nitrogen. To the open and cleaned reactor is charged first the liquid and then the solid reactants. The reactor is closed, purged with CO and then pressurized with CO usually to 20-30 psi. With agitation (750 rpm.) the reactor contents are heated to the desired temperature, usually between 105° and 125° C., in about 45 minutes. Next, the reactor is pressured with CO to the desired pressure, usually between 100 and 200 psi, and repressured after every 30 psi uptake. The reactor is maintained at the desired temperature for a specified time period, usually between 0.5 to 5.0 hours. At the end of the specified time period the reactor contents are normally cooled to 10° C. A vapor phase sample is taken and analyzed by gas chromatography for CO, $H_2$, $CO_2$, and $CH_4$ plus other gaseous hydrocarbons. The reactor gas phase is vented through two dry ice-acetone traps and then a 2.5 gallon saturated solution of calcium hypochlorite to remove iron and/or nickel carbonyls. The reactor is pressurized three times with 90 psia nitrogen and vented through the same trap-vent system.

The reactor contents from the glass pressure bottle or 150 cc autoclave were dumped into a chilled bottle flushed with $N_2$. The liquid proucts were analyzed via a Varian 3700 gas chromatograph equipped with a Supelco DB 1701 30M capillary column or a HP-5880 gas chromatograph equipped with a 1 percent FFAP on Tenax column.

The following examples serve to further illustrate this invention.

EXAMPLE 1

A glass pressure bottle was charged with the following components:

| | |
|---|---|
| $[Rh(CO)_2Cl]_2$ | 0.2 mm |
| $Ph_2PCH_2CH_2P(O)Ph_2$ | 0.4 mm |
| LiI | 3.0 gm |
| $CH_3I$ | 4.56 g |
| Acetic Acid | 2.0 g |
| Methanol | 1.6 g |
| Methyl Acetate | 2.91 g |

Following the procedure of Preparation Example 1 the reaction was carried out at 115° C. and 145 psi total operating pressure. During a 2.5 hr. reaction period 1 mole of CO was consumed per mole of methanol charged. The following organic components were found in the reaction liquid:

| | |
|---|---|
| $CH_3I$ | 4.5 g |
| Methanol | 0.0 g |
| Methyl Acetate | 2.89 g |
| Acetic Acid | 5.0 g |
| $H_2O$ | Trace |

Gas consumption rate was constant throughout the entire time. The selectivity to acetic acid is nearly 100%. The rate is 2.2 $Mhr^{-1}$ and the methanol conversion is 100%.

In this run the methanol conversion was 100%. Methyl acetate was recovered unchanged, i.e., there was no net gain or loss. The water content was extremely low, i.e., less than 0.05 weight percent. This run also demonstrated the use of acetic acid as a solvent.

Similar results are obtained when other rhodium sources are substituted; such as $Rh_2(CO)_4Br_2$, $Rh(CO)_2AcAc^*$ and $K_4Rh_2I_2(SnI_2)_4$ and $[(n-(C_4H_9)_4N][Rh(CO)_2I_2]$.

*=acetylacetonate

EXAMPLE 2

This example illustrates formation of both acetic acid and acetic anhydride.

A glass pressure bottle was charged with the following components:

| | |
|---|---|
| $[Rh(CO)_2Cl]_2$ | 0.2 mm |
| $Ph_2PCH_2CH_2P(O)Ph_2$ | 0.4 mm |
| $CH_3I$ | 4.56 g |
| LiI | 3.0 g |
| Methanol | 0.8 g |
| Methyl Acetate | 5.8 g |

The reaction was carried out for 2.5 hr. at 115° C. and 140 psi total operating pressure. During this period more than 1 mole of CO per mole of methanol charged was consumed. The following components were found in the product mixture via gas chromatography analysis.

| Component | Area % |
|---|---|
| Acetic Acid | 9.5 |
| Methyl Iodide | 19.1 |
| Methyl Acetate | 44.0 |
| Acetic Anhydride | 27.4 |

The rate of gas consumption was constant throughout the entire run. Water and methanol were not detected in the product mixture. The acetic acid rate was 3.1 $Mhr^{-1}$ and the selectivity based on charged methanol was nearly 100%, with methanol conversion also 100%. The acetic anhydride rate was also 3.1 $Mhr^{-1}$.

EXAMPLE 3

Following the procedure of Example 1 a reaction was carried out with various amounts of reaction components. The results are summarized below (All runs: MEOH=0.8 g, MeOAc=5.8 g, 115° C., 145 psi):

| Rh mm | LiI gm | $CH_3I$ gm | $Ph_2PCH_2CH_2P(O)Ph_2$ mm | Rate of Acetic Acid $Mhr^{-1}$ |
|---|---|---|---|---|
| 0.4 | 2.25 | 4.56 | 0.4 | 2.8 |
| 0.4 | 1.5 | 4.56 | 0.4 | 4.0 |
| 0.4 | 0.75 | 4.56 | 0.4 | 2.4 |
| 0.4 | 1.5 | 6.84 | 0.4 | 3.1 |
| 0.2 | 1.5 | 4.56 | 0.2 | 2.4 |
| 0.4 | 1.5 | 2.28 | 1.2 | 5.7 |
| 0.4 | 1.5 | 2.28 | 0.4 | 5.8 |

In all cases the methanol conversion was 100% and less than 0.05% water was detected in the product mixture. The rate of gas consumption was constant throughout the entire reaction. This example demonstrates that various amounts of LiI and $CH_3I$ can be utilized. When other halide promoters are substituted for $CH_3I$, such as hydriodic acid, ethyl iodide, trimethyl ammonium iodide, methyl bromide and the like, similar results are obtained.

EXAMPLE 4

Several runs were carried out at different reaction times in order to observe the product mixture as a function of time. In each case the following components were initially used:

| | |
|---|---|
| [Rh(CO)$_2$Cl]$_2$ | 0.2 mm |
| Ph$_2$PCH$_2$CH$_2$P(O)Ph$_2$ | 0.4 mm |
| CH$_3$I | 4.58 g |
| LiI | 1.5 gm |
| Methanol | 0.8 g |
| Methyl Acetate | 5.8 g |

The reaction conditions are the same as in Example 2. The results are summarized below.

| Run | Reaction Time Hr. | Product Mixture, Wt. % | | | | | |
|---|---|---|---|---|---|---|---|
| | | H$_2$O | HoAc | CH$_3$OH | CH$_3$I | MeOAc | Ac$_2$O |
| 1 | 0.26 | 2.3 | 0.4 | 0.4 | 37 | 58 | 0 |
| 2 | 0.67 | 0.3 | 12.5 | 0.0 | 38 | 48 | 0.1 |
| 3 | 1.7 | 0.0 | 12.1 | 0 | 38 | 37 | 11.0 |

This example shows the effect of reaction time on product distribution. In Run 1 most of the methanol was converted to methyl acetate because insufficient CO was consumed. The water level is high. In Run 2 one mole of CO per mole of methanol charged was consumed and all the methanol has been converted to essentially anhydrous acetic acid. In Run 3 more than 1 mole of CO was consumed per mole of methanol charged and this resulted in a product containing a mixture of essentially anhydrous acetic acid and acetic anhydride.

EXAMPLE 5

A run was carried out in accordance with Example 1 except that LiI was not utilized. In this case no further reaction was observed after the consumption of 0.75 mole of CO per mole of methanol charged. During the reaction the rate of gas uptake was not constant; it slowed markedly and finally stopped. The acetic acid rate was approximately 1.0 Mhr$^{-1}$ during the initial part of the reaction. The product mixture was not homogeneous, i.e., a noticeable amount of catalyst precipitation was present.

This example demonstrates the importance of the metal halide, LiI. Without its use the methanol conversion is low, the conversion rate is low and the reaction mixture is no longer homogeneous.

EXAMPLE 6

A run was carried out in accordance with the procedure of Example 1 except bis(1,2-diphenylphosphino)ethane, Ph$_2$PCH$_2$CH$_2$PPh$_2$ (0.5 mm) was used in place of Ph$_2$PCH$_2$CH$_2$P(O)Ph$_2$. In this case at 115° C. and 145 psi total operating pressure there was no observable reaction. Gas was not consumed and acetic acid was not observed in the reaction mixture. Ligands such as Ph$_2$PCH$_2$CH$_2$PPh$_2$ are disclosed in U.K. Specification No. 1,584,740. As shown above, Ph$_2$PCH$_2$CH$_2$PPh$_2$ will not serve as a ligand under the instant reaction conditions.

EXAMPLE 7

A run was carried out in accordance with Example 2 except Ph$_2$PCH$_2$CH$_2$P(O)Ph$_2$ was not utilized. Carbon monoxide consumption was not constant and no further reaction was observed after consumption of about 0.82 mole of CO per mole of methanol charged. The rate to acetic acid was approximately 1.0 Mhr$^{-1}$ during the initial part of the reaction.

This example demonstrates the importance of using a R$_1$R$_1$P(CH$_2$)$_n$P(O)R$_1$R$_1$ type ligand. With its use high rate to acetic acid and 100% methanol conversion is possible. When other ligands such as Ph$_2$P(CH$_2$)$_2$COCH$_2$CH$_3$; (CH$_3$)$_2$P(CH$_2$)$_3$P(O)(CH$_3$)$_2$; (Tolyl)$_2$P(CH$_2$)$_2$C(O)OCH$_2$CH$_3$ and (Benzyl)$_2$P(CH$_2$)$_2$-P(O) (Benzyl)$_2$ are substituted for the ligand of Example 7, similar results are obtained.

The experimental findings are unexpected in view of the disclosure by R. T. Eby and T. C. Singleton in "Applied Industrial Catalysis", Vol. I, Chapter 10, page 281, *Academic Press*, NYC (1983). In Chapter 10, entitled "Methanol Carbonylation to Acetic Acid", the authors state: "Iodide salts of alkali metals are inactive as catalysts in the rhodium-catalysed carbonylation of methanol, even though the [Rh(CO)$_2$I$_2$] complex is formed in the presence of alkali metal iodides."

EXAMPLE 8

A 150 cc autoclave was charge with the following components:

| | |
|---|---|
| Rh(CO)$_2$AcAc$^a$ | 3 mm |
| Ph$_2$PCH$_2$CH$_2$P(O)Ph$_2$ | 3 mm |
| LiI | 111 mm |
| CH$_3$I | 272 mm |
| CH$_3$OH | 7.91 g |
| Methyl Acetate | 39 g |
| Acetic Acid | 10 g |

This reaction was carried out at 115° C. and 145 psi operating pressure for 2.0 hrs. After 2.0 hrs a considerable amount of gas was consumed. The reactor was cooled and the resulting liquid mixture was analyzed via gas chromatography. The following components were found:

| | Wt % |
|---|---|
| H$_2$O | 0.05 |
| Acetic Acid | 26.4 |
| CH$_3$OH | 0 |
| CH$_3$I | 40 |
| Methyl Acetate | 21 |
| Acetic Anhydride | 11.4 |

The rate to acetic acid was 2.5 Mhr$^{-1}$.

EXAMPLE 9

Preparation of Complexes

A series of runs was performed using the following general procedure to produce the complexes of formulas A' and B'. A solution of 2.5 millimoles (mm) of C$_6$H$_5$PCH$_2$P(O) (C$_6$H$_5$)$_2$ in 10 ml methylene chloride was added to a solution of 1.25 mm [Rh(CO)$_2$Cl]$_2$ in 10 ml methylene chloride. The mixture was allowed to stir for 10 minutes and the methylene chloride was removed under vacuum. The residual viscous oil was redissolved in 10 ml methylene chloride and the solvent evaporated again. This procedure was repeated three to four times.

The residue from the final evacuation was dissolved in 5 ml methylene chloride. Yellow crystals precipitated upon standing. The crystals were filtered, washed with methylene chloride and dried under vacuum. X-ray crystallographic analysis showed that the compound corresponds to:

cis-RhCl(CO)[(C$_6$H$_5$)$_2$PCH$_2$P(O)(C$_6$H$_5$)$_2$]·CH$_2$Cl$_2$, which contains a Rh to O bond. The infrared spectrum displayed a single intense bond at 1990 cm$^{-1}$ due to the presence of coordinated CO to Rh in the complex.

The above procedure was followed exactly using (C$_6$H$_5$)$_2$P(CH$_2$)$_n$P(O) (C$_6$H$_5$)$_2$; in which n was 2, 3 and 4 and for (C$_6$H$_5$)$_2$P(CH$_2$)$_n$ C(O)OC$_2$H$_5$ in which n was 2. In all instances yellow crystals were recovered which gave infrared spectra similar to the first complex described above, having an intense band at 1990 cm$^{-1}$ indicating the formation of the similar structure. The complex products produced had the formulas:

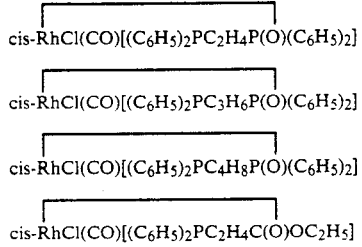

cis-RhCl(CO)[(C$_6$H$_5$)$_2$PC$_2$H$_4$P(O)(C$_6$H$_5$)$_2$]

cis-RhCl(CO)[(C$_6$H$_5$)$_2$PC$_3$H$_6$P(O)(C$_6$H$_5$)$_2$]

cis-RhCl(CO)[(C$_6$H$_5$)$_2$PC$_4$H$_8$P(O)(C$_6$H$_5$)$_2$]

cis-RhCl(CO)[(C$_6$H$_5$)$_2$PC$_2$H$_4$C(O)OC$_2$H$_5$]

The dicarbonyl compounds of the above were prepared by reacting a portion of each of the above monocarbonyl compounds, respectively under CO pressure. Infrared spectra showed the formation of the dicarbonyl compounds had been achieved by the presence of two intense bands, typically at 2090 cm$^{-1}$ and 2010 cm$^{-1}$.

We claim:

1. Process for the production of organic carboxylic acids of the formula RCOOH and carboxylic acid anhydrides of the formula RC(O)O(O)CR which comprises catalytically reacting an alcohol, which is methanol or a mixture of methanol and at least one higher alcohol selected from the group consisting of ethanol and propanol, carbon monoxide, and an organic ester of the formula RC(O)OR or a compound which, under the reaction conditions, can be converted to said organic ester, in contact with a homogeneous catalyst system consisting essentially of (a) a rhodium component selected from the group consisting of rhodium metal and a rhodium compound, (b) lithium iodide, potassium iodide or sodium iodide, and (c) a phosphorus containing ligand in which there is present at least one oxo oxygen atom attached to a phosphorus atom or a carbon atom to form a Z group and in which the

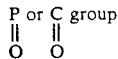

P or C group in Z group is located at least one carbon atom removed from the phosphorus atom of the molecules represented by the formulas

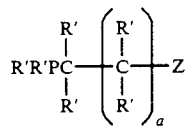

or

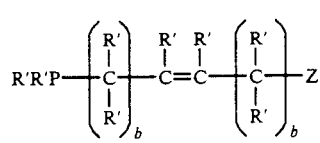

wherein R is an alkyl group having from 1 to 3 carbons; R' is H—, an aryl group having from 6 to 10 ring carbon atoms and any alkyl moiety thereof having from 1 to 10 carbon atoms, or an aralkyl group having 6 to 10 ring carbons with from 1 to 10 carbon atoms in the alk-moiety thereof, or an alkyl group having from 1 to 10 carbon atoms; and wherein one or more of said R' groups can be substituted with a Z group but not more than 3 of said R' groups in the molecule are so substituted; where a is an integer from 0 to 4, b is an integer from 0 to 3, and Z is a member selected from the group consisting of

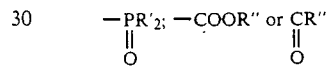

—PR'$_2$; —COOR" or CR"

wherein R" is R' and said reaction is carried out at a reaction temperature of up to about 170° C. and a reaction pressure of up to about 450 psig.

2. The process as claimed in claim 1 wherein catalyst component (b) is lithium iodide.

3. The process as claimed in claim 1 wherein the mole ratio of rhodium to ligand is from about 3:1 to 1:1.

4. The process as claimed in claim 1 wherein RC(O)OR is methyl acetate.

5. The process as claimed in claim 1 wherein R' is phenyl.

6. The process as claimed in claim 1 wherein the volume ratio of alcohol to RC(O)OR is from about 100:1 to 1:100.

7. The process as claimed in claim 1 wherein the alcohol is methanol.

8. The process as claimed in claim 1 wherein the ligand is Ph$_2$P(CH$_2$)$_2$ P(O)Ph$_2$, wherein Ph is phenyl.

9. The process as claimed in claim 1 in which acetic acid is employed as a reaction solvent.

10. The process as claimed in claim 1 wherein the rhodium component is supplied as a rhodium carbonyl compound.

11. The process as claimed in claim 1 wherein the reaction temperature is from about 105° to 150° C.

12. The process as claimed in claim 1 wherein the reaction temperature is from about 105° to 150° C.

13. The process as claimed in claim 1 wherein the reaction pressure is from about 100 to 400 psig.

14. The process as claimed in claim 1 wherein Z is

—PR'R'.

15. The process as claimed in claim 1 wherein Z is —COOR".

16. The process as claimed in claim 1 wherein Z is —C(O)R".

17. Process for the producton of organic carboxylic acids of the formula RCOOH and carboxylic acid anhydrides of the formula RC(O)O(O)CR which comprises catalytically reacting an alcohol which is methanol or a mixture of methanol and at least one higher alcohol selected from the group consisting of ethanol and propanol, carbon monoxide, and an organic ester of the formula RC(O)OR or a compound which, under the reaction conditions, can be converted to said organic ester, in contact with a homogeneous catalyst system consisting essentially of (a) a rhodium component selected from the group consisting of rhodium metal and a rhodium compound, (b) lithium iodide, potassium iodide or sodium iodide, (c) a halide promoter, and (d) a phosphorus containing ligand in which there is present at least one oxo oxygen atom attached to a phosphorus atom or a carbon atom to form a Z group and in which the

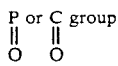

in Z group is located at least one carbon atom removed from the phosphorus atom of the molecules represented by the formulas

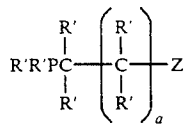

or

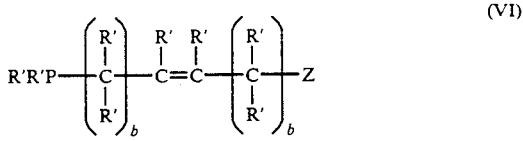

wherein R is an alkyl group having from 1 to 3 carbons; R' is H, an aryl group having from 6 to 10 ring carbon atoms and any alkyl moiety thereof having from 1 to 10 carbon atoms, or an aralkyl group having 6 to 10 ring carbons with from 1 to 10 carbon atoms in the alk-moiety thereof, or an alkyl-group having from 1 to 10 carbon atoms; and wherein one or more of said R' groups can be substituted with a Z group but not more than 3 of said R' groups in the molecule are so substituted; where a is an integer from 0 to 4, b is an integer from 0 to 3, and Z is a member selected from the group consisting of

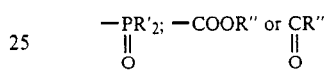

wherein R" is R' and said reaction is carried out at a reaction temperature of up to about 170° C. and a reaction pressure of up to about 450 psig.

18. The process as claimed in claim 17 wherein halide promoter (d) is methyl iodide and catalyst component (b) is lithium iodide.

19. The process as claimed in claim 18 wherein the mole ratio of LiI:Rh is from about 128:1 to 1:1.

20. The process as claimed in claim 19 wherein the mole ratio of LiI:CH$_3$I is from about 10:1 to 1:10.

* * * * *

UNITED STATES PATENT AND TRADEMARK OFFICE
CERTIFICATE OF CORRECTION

PATENT NO. : 5,026,907

DATED : June 25, 1991

INVENTOR(S) : R. W. Wegman, et al.

It is certified that error appears in the above-identified patent and that said Letters Patent is hereby corrected as shown below:

Column 18:
 Claim 11, line 58, "105° to 150°C" should read --50° to 160°C--.

Signed and Sealed this

Seventh Day of June, 1994

Attest:

BRUCE LEHMAN

Attesting Officer          Commissioner of Patents and Trademarks